United States Patent
Edwards et al.

(10) Patent No.: US 11,517,341 B2
(45) Date of Patent: Dec. 6, 2022

(54) METHODS OF RECIPROCATION IN A SURGICAL SHAVER

(71) Applicant: Gyrus ACMI, Inc., Southborough, MA (US)

(72) Inventors: Kevin Edwards, Olive Branch, MS (US); Ahmad Alsaffar, Bartlett, TN (US); Joel Willhite, Memphis, TN (US); David Church, Millington, TN (US); Daniel Goldberg, Germantown, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 278 days.

(21) Appl. No.: 16/282,505

(22) Filed: Feb. 22, 2019

(65) Prior Publication Data

US 2020/0268400 A1 Aug. 27, 2020

(51) Int. Cl.
A61B 17/32 (2006.01)

(52) U.S. Cl.
CPC .......... *A61B 17/32002* (2013.01); *A61B 2017/32004* (2013.01); *A61B 2017/320024* (2013.01); *A61B 2017/320028* (2013.01)

(58) Field of Classification Search
CPC .... A61B 17/32002; A61B 2017/32004; A61B 2017/320024; A61B 2017/320028; A61B 17/320783; A61B 2017/00398; A61B 17/32; A61B 2017/320004; A61B 2017/320008; A61B 2017/320012; A61B 2017/320016; A61B 2017/320032; A61B 17/320036
See application file for complete search history.

(56) References Cited

U.S. PATENT DOCUMENTS

| | | |
|---|---|---|
| 4,940,468 A | 7/1990 | Petillo |
| 6,156,049 A | 12/2000 | Lovato et al. |
| 6,258,111 B1 * | 7/2001 | Ross ............... A61B 17/32002 606/171 |
| 6,342,061 B1 | 1/2002 | Kauker et al. |
| 11,141,182 B2 | 10/2021 | Goldberg et al. |
| 11,147,579 B2 | 10/2021 | Edwards et al. |

(Continued)

FOREIGN PATENT DOCUMENTS

| | | |
|---|---|---|
| EP | 3698737 A1 | 8/2020 |
| JP | 2005507703 A | 3/2005 |
| JP | 2017529940 A | 10/2017 |

OTHER PUBLICATIONS

Wikipedia contributors. "Scotch yoke." Wikipedia, The Free Encyclopedia. Wikipedia, The Free Encyclopedia, Apr. 1, 2019. Web. May 29, 2019, 3 pages.

(Continued)

*Primary Examiner* — Katherine H Schwiker
*Assistant Examiner* — Raihan R Khandker
(74) *Attorney, Agent, or Firm* — Schwegman Lundberg & Woessner, P.A.

(57) ABSTRACT

Disclosed herein is a medical device. The medical device includes a blade tube section, a solenoid, and a mechanical arrangement. The blade tube section includes an outer blade tube, an inner blade tube, and a cutting window at a distal end of the blade tube section. The solenoid is offset from a central axis of the blade tube section. The mechanical arrangement is between the inner blade tube and the solenoid.

12 Claims, 5 Drawing Sheets

(56) References Cited

U.S. PATENT DOCUMENTS

| | | | |
|---|---|---|---|
| 11,213,312 B2 | 1/2022 | Edwards et al. | |
| 2002/0183851 A1 | 12/2002 | Spiegelberg et al. | |
| 2003/0009888 A1* | 1/2003 | Marinkovich | B23D 51/16 30/394 |
| 2003/0083684 A1 | 5/2003 | Cesarini et al. | |
| 2005/0005458 A1 | 1/2005 | Marinkovich et al. | |
| 2006/0096104 A1* | 5/2006 | Neitzell | B23D 51/16 30/393 |
| 2007/0282344 A1 | 12/2007 | Yedlicka et al. | |
| 2009/0270893 A1 | 10/2009 | Arcenio | |
| 2011/0028898 A1 | 2/2011 | Clark, III et al. | |
| 2011/0247847 A1* | 10/2011 | Holmes | B27B 19/09 173/19 |
| 2013/0211321 A1 | 8/2013 | Dubois et al. | |
| 2015/0090058 A1 | 4/2015 | Roschke et al. | |
| 2016/0331645 A1 | 11/2016 | Bagwell et al. | |
| 2017/0231654 A1 | 8/2017 | Cesarini et al. | |
| 2018/0146974 A1* | 5/2018 | Bjursten | A61B 17/22 |
| 2019/0070215 A1 | 3/2019 | Perry et al. | |
| 2020/0268401 A1 | 8/2020 | Edwards et al. | |
| 2020/0268402 A1 | 8/2020 | Edwards et al. | |
| 2020/0268946 A1 | 8/2020 | Wood | |
| 2020/0275944 A1 | 9/2020 | Goldberg et al. | |

OTHER PUBLICATIONS

Wikipedia contributors. "Driving wheel," Wikipedia, The Free Encyclopedia. Wikipedia, The Free Encyclopedia, Apr. 4, 2019. Web. May 22, 2019, 4 pages.

"U.S. Appl. No. 16/286,748, Final Office Action dated Oct. 1, 2020", 12 pgs.

"U.S. Appl. No. 16/286,748, Non Final Office Action dated Jun. 16, 2020", 13 pgs.

"U.S. Appl. No. 16/286,748, Response filed Jan. 4, 2021 to Final Office Action dated Oct. 1, 2020", 14 pgs.

"U.S. Appl. No. 16/286,748, Response fifed Sep. 16, 2020 to Non Final Office Action dated Jun. 16, 2020", 13 pgs.

"U.S. Appl. No. 16/287,329, Non Final Office Action dated Nov. 20, 2020", 14 pgs.

"U.S. Appl. No. 16/290,047, Advisory Action dated Jan. 8, 2021", 3 pgs.

"U.S. Appl. No. 16/290,047, Final Office Action dated Oct. 20, 2020", 11 pgs.

"U.S. Appl. No. 16/290,047, Non Final Office Action dated Jun. 16, 2020", 13 pgs.

"U.S. Appl. No. 16/290,047, Response filed Jan. 15, 2021 to Advisory Action dated Jan. 8, 2021", 10 pgs.

"U.S. Appl. No. 16/290,047, Response filed Sep. 16, 2020 to Non Final Office Action dated Jun. 16, 2020", 10 pgs.

"U.S. Appl. No. 16/290,047, Response filed Dec. 10, 2020 to Final Office Action dated Oct. 20, 2020", 9 pgs.

"European Application Serial No. 20158861.3, Extended European Search Report dated Jun. 29, 2020", 7 pgs.

"U.S. Appl. No. 16/286,748, Non Final Office Action dated Apr. 27, 2021", 15 pgs.

"U.S. Appl. No. 16/286,748, Response filed Jul. 27, 2021 to Non Final Office Action dated Apr. 27, 2021", 12 pgs.

"U.S. Appl. No. 16/287,329, Corrected Notice of Allowability dated Jun. 21, 2021", 2 pgs.

"U.S. Appl. No. 16/287,329, Notice of Allowance dated Jun. 11, 2021", 8 pgs.

"U.S. Appl. No. 16/287,329, Response filed Feb. 22, 2021 to Non Final Office Action dated Nov. 20, 2020", 12 pgs.

"U.S. Appl. No. 16/290,047, Corrected Notice of Allowability dated Jun. 30, 2021", 3 pgs.

"U.S. Appl. No. 16/290,047, Corrected Notice of Allowability dated Jul. 12, 2021", 2 pgs.

"U.S. Appl. No. 16/290,047, Notice of Allowance dated Jun. 23, 2021", 6 pgs.

"European Application Serial No. 20158861.3, Response filed Feb. 25, 2021 to Extended European Search Report dated Jun. 29, 2020", 9 pgs.

"Japanese Application Serial No. 2020-28522, Response filed Jun. 15, 2021 to Office Action dated Mar. 15, 2021", w/ English Claims, 7 pgs.

"Japanese Application Serial No. 2020-28552, Notification of Reasons for Refusal dated Mar. 15, 2021", with English translation, 14 pgs.

U.S. Appl. No. 16/286,748, filed Feb. 27, 2019, Methods of Reciprocation in a Surgical Shaver.

U.S. Appl. No. 16/290,047, filed Mar. 1, 2019, Methods of Reciprocation in a Surgical Shaver.

U.S. Appl. No. 16/287,329, filed Feb. 27, 2019, Methods of Reciprocation in a Surgical Shaver.

"U.S. Appl. No. 16/286,748, Corrected Notice of Allowability dated Sep. 15, 2021", 2 pgs.

"U.S. Appl. No. 16/286,748, Notice of Allowance dated Sep. 2, 2021", 5 pgs.

"U.S. Appl. No. 16/287,329, Corrected Notice of Allowability dated Sep. 15, 2021", 2 pgs.

"U.S. Appl. No. 16/290,047, Corrected Notice of Allowability dated Sep. 16, 2021", 2 pgs.

"U.S. Appl. No. 16/286,748, Corrected Notice of Allowability dated Dec. 7, 2021", 2 pgs.

"Japanese Application Serial No. 2020-028552, Final Notification of Reasons for Refusal dated Aug. 23, 2021", w/ English Translation, 4 pgs.

* cited by examiner

METHODS OF RECIPROCATION IN A SURGICAL SHAVER

BACKGROUND

Field of the Invention

The invention relates to a medical device and more specifically relates to methods of reciprocation for a surgical shaver device.

Brief Description of Prior Developments

Conventional surgical shavers generally use a rotational motor coupled with a parallel gear train to impart oscillatory motion on the shaver blades. However, using the oscillating motion to cut can tear and strip mucosa. Reciprocating blades, on the other hand, can create cleaner, more precise cuts.

Reciprocating surgical shavers exist in the market, however these devices generally use air pressure from a vacuum to drive the reciprocation, which can result in a weak cutting stroke and in turn make the device unable to cut through the tissue necessary to complete a procedure.

Accordingly, there is a need to provide improved and reliable medical device configurations having reciprocating blades.

SUMMARY

In accordance with one aspect of the invention, a medical device is disclosed. The medical device includes a blade tube section, a solenoid, and a mechanical arrangement. The blade tube section includes an outer blade tube, an inner blade tube, and a cutting window at a distal end of the blade tube section. The solenoid is offset from a central axis of the blade tube section. The mechanical arrangement is between the inner blade tube and the solenoid.

In accordance with another aspect of the invention, a medical device is disclosed. The medical device includes a blade tube section, a solenoid, and a lever member. The blade tube section includes an outer blade tube, an inner blade tube, and a cutting window at a distal end of the blade tube section. The lever member is connected to the inner blade tube and the solenoid.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
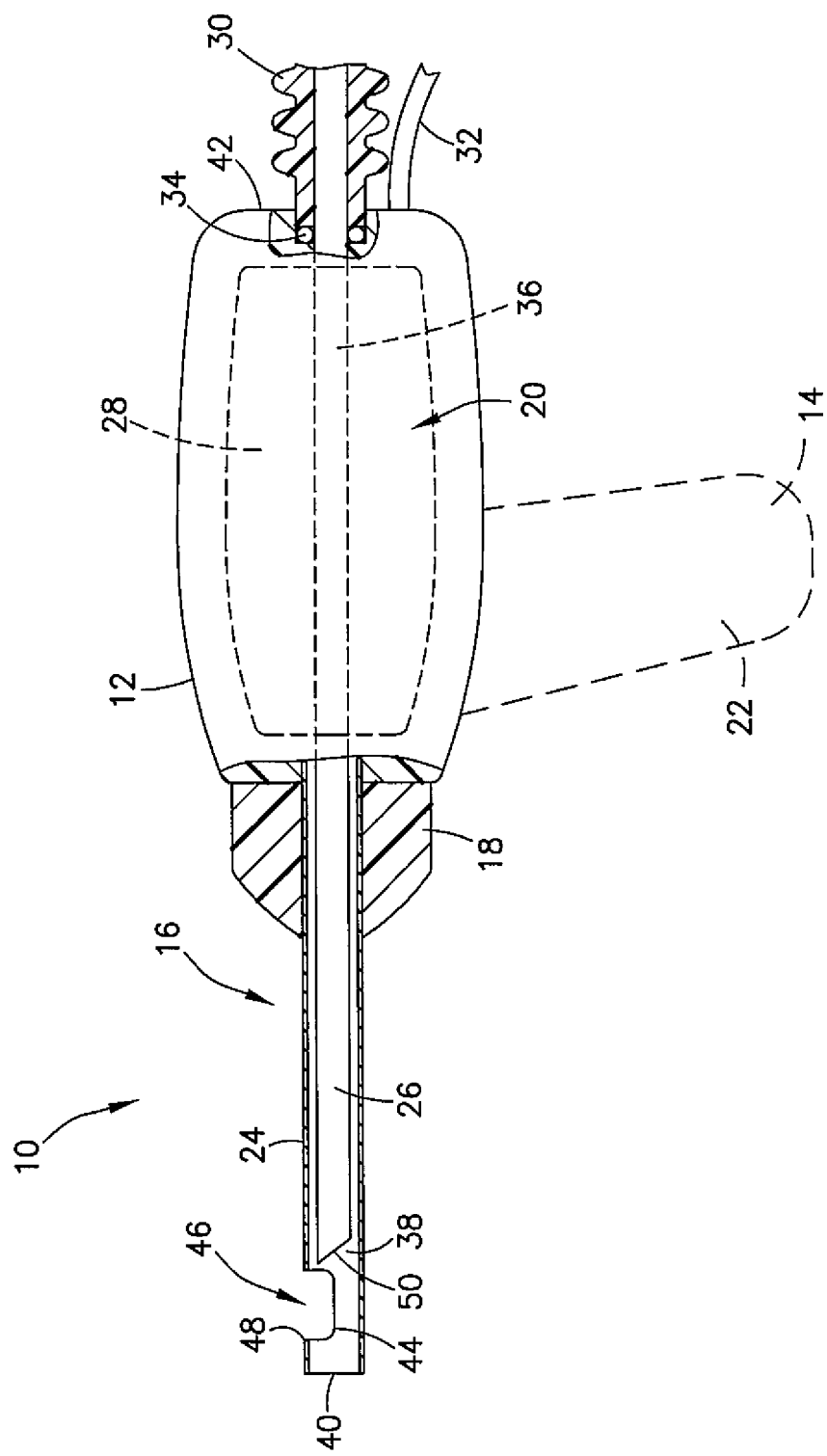
FIG. 1 is a side view of a medical device incorporating features of the invention.
Figure 3:
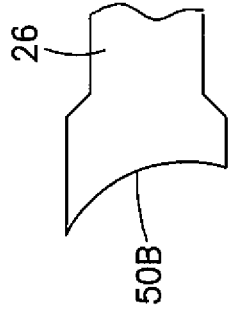
FIG. 3 is an alternate embodiment of a cutting tip used in the medical device shown in FIG. 1.
Figure 5:
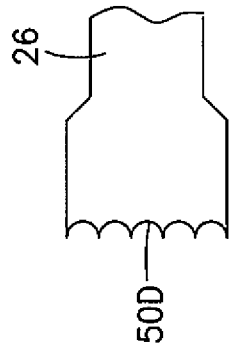
FIG. 5 is an alternate embodiment of a cutting tip used in the medical device shown in FIG. 1.
Figure 2:
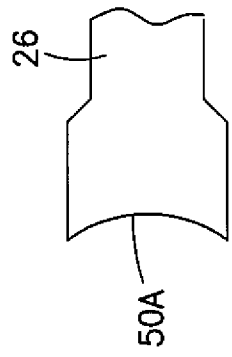
FIG. 2 is an alternate embodiment of a cutting tip used in the medical device shown in FIG. 1.
Figure 4:
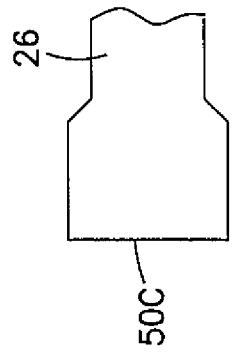
FIG. 4 is an alternate embodiment of a cutting tip used in the medical device shown in FIG. 1.

Referring to FIG. 1, there is shown a perspective view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is generally configured for use in the removal of nasal polyps, sub-mucosal debulk of turbinates, and functional endoscopic sinus surgery (FESS).

The medical device 10, which may be a disposable debrider for example, comprises a housing 12 (which may have a pistol grip portion 14), a blade tube section 16, and a nosepiece 18. The nosepiece 18 may be a rotatable nosepiece and is between the housing 12 and the blade tube section 16. However, it should be noted that exemplary embodiments of the medical device may comprise any suitable configuration such as configurations having a nosecone coupled to an outer member (of the housing), or any other suitable curved or straight debrider configuration which may comprise an irrigation feature, for example. The blade tube section 16 of the device 10 can be configured with large and small shaver tubes, depending on anatomy and surgeon preference, and can also be adapted for bipolar or monopolar radio-frequency (RF) power. An external ESG (electrosurgical generator) may supply the RF power, for example.

The housing 12 comprises an interior cavity 20 sized and shaped to house actuation members of the device 10. Additionally, in some embodiments the optional pistol grip portion 14 may include an interior cavity 22 which can also be sized and shaped to house actuation members (or other hardware) of the device 10.

The blade tube section 16 comprises an outer blade tube 24 and an inner blade tube 26, and the medical device 10 further comprises a blade drive system 28 mounted within the cavity 20 (or mounted within the cavity 22) which is configured to drive the inner blade tube 26. It should be noted that in some embodiments, the blade tubes 24, 26 may comprise flexible and/or curved tubes.

Additionally, the medical device 10 comprises a connector 30 and a power cable 32. The connector (or suction connection) 30 is configured to connect to a suction tube or a vacuum source. The connector 30 includes a dynamic seal 34 mounted inside of the connector 30. The dynamic seal 34 is configured to provide a sealed interface between the connector 30 and an inner lumen 36 (via the outer surface of the inner blade tube 26) of the inner blade tube 26. The power cable 32 is configured to provide power to components(s) of the blade drive system 28.

The outer blade tube 24 is (rotatably or fixedly) mounted to the housing 12 and acts as a static member. For example, according to various exemplary embodiments, the nosepiece 18 can be mounted to the outer blade tube 24 and can optionally rotate the outer blade tube 24 independent of the housing 12. The inner blade tube 26 is slidably mounted inside the outer blade tube (such that the inner blade tube 26 is slideably mounted within a lumen 38 of the outer blade tube 24).

The inner blade tube 26 is configured to be forced distally [i.e. towards the distal end 40] or proximally [i.e. towards the proximal end 42] by the blade drive system 28. The outer blade tube 24 comprises an opening 44 proximate the distal end 40 which forms a cutting window 46 for the medical device 10. The cutting window 46 is formed by a cutting edge 48 of the outer blade tube (i.e. the distal edge of the opening 44) and a cutting tip 50 of the inner blade tube 26. The reciprocal motion of the inner blade tube 26 provides for the cutting tip 50 to reciprocate relative to the cutting edge 48 to perform tissue cuts (i.e. by bringing the cutting tip 50 into alignment and out of alignment with the opening 44 of the outer blade tube 24). In the embodiment shown in FIG. 1, the cutting edge 48 is at the cylindrical face portion of the cutting window 46. However in alternate embodiments, the cutting edge may be provided at any suitable location along the distal end 40.

It should be noted that although various exemplary embodiments of the invention have been described in connection with the cutting tip 50 comprising an angled straight edge configuration, alternate embodiments may comprise other suitable configurations. For example, FIGS. 2-5 illustrate alternate embodiments for the cutting tip 50 (see cutting tips 50A, 50B, 500, 50D).

Figure 6:
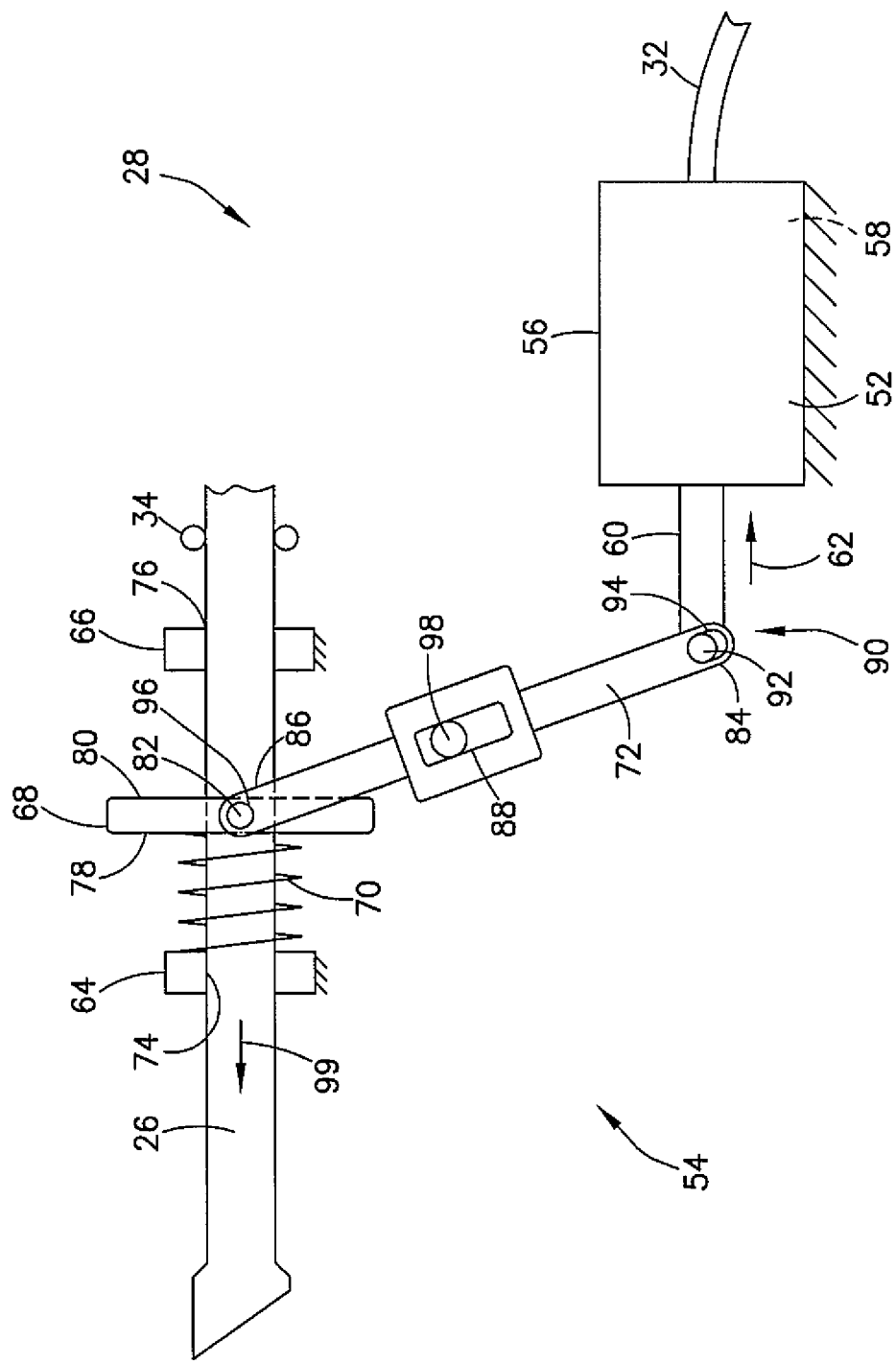
FIG. 6 is a side view of a blade drive system used in the medical device shown in FIG. 1.

Referring now also to FIG. 6, the blade drive system 28 comprises a solenoid 52 and a mechanical arrangement 54. The solenoid 52 is offset from a central axis of the blade tube section 16. The solenoid 52 generally comprises a static hollow cylindrical section 56 with an energizing coil 58, and a shaft 60 (connected to an armature in the center of the hollow static section 56) that is inducted to move axially (see direction 62) with a known force when the coil 58 is electrically, energized (by power cable 32).

The mechanical arrangement 54 comprises a distal bushing 64, a proximal bushing 66, a collar 68, a spring 70, and a lever member 72. The bushings 64, 66 are fixedly mounted to the housing 12 and each comprise an opening 74, 76 sized and shaped to allow reciprocation of the inner blade tube 26 therethrough. The collar 68 comprises a general flange shape and has a first side 78 and a second side 80 and is between the bushings 64, 66. The collar 68 further comprises a pin (or boss feature) 82 between the first and second sides 78, 80. The collar 68 is also fixedly connected (or fixedly mounted) to the inner blade tube 26. The spring 70 is between the distal bushing 64 and the first side 78 of the collar 68. According to various exemplary embodiments, the spring is a compression spring, however in alternate embodiments the spring may be an extension spring. Additionally, in some further embodiments, the spring may be between the proximate bushing 66 and the second side 80 of the collar 68.

The lever member 72 comprises a first end 84, an opposite second end 86, and an opening 88 between the first end 84 and the second end 86. The first end 84 of the lever member is movably connected to the shaft 60 of the solenoid 52 at mount point 90. According to various exemplary embodiments, the mount point 90 comprises a pin (or boss feature) 92 on the shaft 60 and an opening 94 (which receives the pin [or boss feature]) at the first end 84 of the lever member 72. In this embodiment, the opening 94 comprises an elongated or slotted shape to provide a movable connection between the opening 94 and the pin 92. However, in alternate embodiments any other suitable feature, which allows for a movable connection between the lever member and the shaft can be provided. According to various exemplary embodiments, the mount point can be fixed to push & pull, 'push' only, or 'pull' only, depending on the direction of the power stroke of the solenoid and/or the solenoid configuration. The second end 86 of the lever member 72 comprises an opening 96 sized and shaped to receive the pin 82 of the collar which together provides for a movable connection between the lever member 72 and the collar 68. However, in alternate embodiments any other suitable feature, which allows for a movable connection between the lever member and the collar can be provided. According to some embodiments, the opening 96 comprises an elongated or slotted shape.

The opening 88 is sized and shaped to receive a pin (or boss feature) 98 fixedly mounted to the housing 12. According to some embodiments, the opening 88 comprises an elongated or slotted shape. The movable connection between the opening 88 and the pin 98 allows for the lever member 72 to pivot (or rotate) about the pin 98.

The mechanical arrangement described above is configured to have the lever member 72 rotate (and/or slide) about the fixed pin 98 to transfer solenoid actuation to the inner blade tube 26. According to various exemplary embodiments, the 'reverse' solenoid motion (i.e. power stroke of solenoid 52 in direction 62) creates a forward motion (see arrow 99) of the inner blade tube 26. For example, when the solenoid 52 is actuated, the shaft 60 moves in direction 62, which causes the lever arm 72 to pivot or rotate in a counter clockwise direction, which further causes the inner blade tube 26 to move in direction 99. The compression spring 70 is then configured to provide a biasing force in the opposite direction (i.e. opposite of direction 99) to move the inner blade tube 26 (in the direction opposite of 99) and cause a clockwise pivot or rotation of the lever member 72, which returns the shaft 60 of the solenoid 52 in the reverse stroke (i.e. moves the shaft 60 in the direction opposite of 62). This movement of the inner blade tube 26 in the direction 99 and opposite of the direction 99 provides reciprocating motion of the inner blade tube within the outer blade tube.

Although the embodiment above has been described in connection with a 'reverse' solenoid motion (i.e. power stroke of solenoid 52 in direction 62), alternate embodiments may be provided with a power stroke in the opposite direction and an extension spring (in place of the compression spring 70), or a compression spring between the collar 68 and the proximal bushing 66.

It should be noted that in various exemplary embodiments, the pin 98 can be placed in different locations to create different stroke lengths and mechanical force efficiencies relative to the stroke and force of the solenoid. Additionally, it should further be noted that in this embodiment the openings 88, 94 have been described as having a slotted or elongated shape to provide "de-constrained" connections to pins 98, 92 while the connection between pin 82 and opening 96 provides for a substantially fixed pivot point. With this configuration the lever member 72 provides a swinging arc and a single fixed pivot point (at the movable connection between the pin 82 and the opening 96) and "de-constrained" connections (which move in x and y directions relative to the swinging arc [via the elongated/slotted openings 88, 94]) at pins 98, 92. However in alternate embodiments, the fixed pivot point could instead be provided at pin 98 or 92 with the "de-constrained" connections at the remaining two openings 88, 94, 96.

Figure 7:
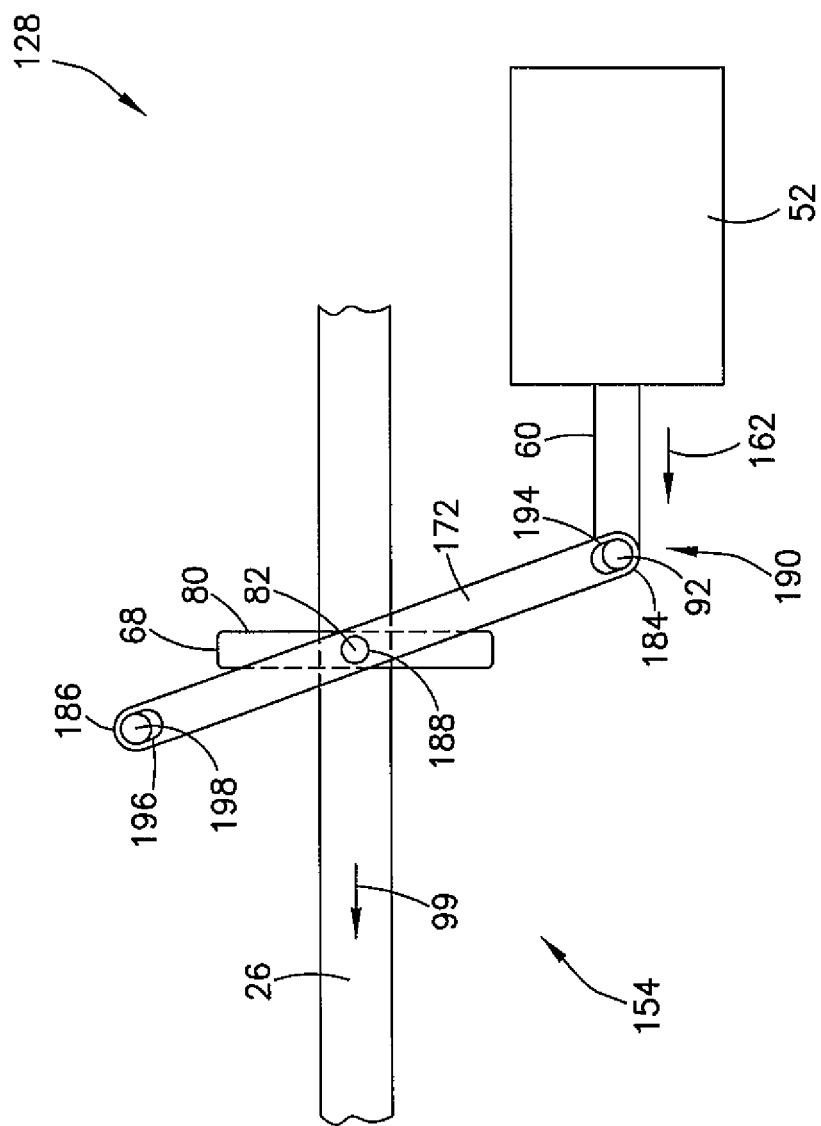
FIG. 7 is a side view of an alternate blade drive system used in the medical device shown in FIG. 1.

Referring now also to FIG. 7, an alternate embodiment of a blade drive system 128 is shown. The blade drive system 128 is similar to the blade drive system 28 and similar features are similarly numbered. Similar to the mechanical arrangement 54, the mechanical arrangement 154 comprises a lever member 172 having a first end 184, an opposite second end 186, and an opening 188 between the first end 184 and the second end 186. Also similarly the first end 184 of the lever member is movably connected to the shaft 60 of the solenoid 52 at mount point 190 comprising the pin (or boss feature) 92 on the shaft 60 and an opening 194 (which receives the pin [or boss feature]) at the first end 184 of the lever member 172. The opening 194 comprises an elongated or slotted shape to provide a movable connection between the opening 194 and the pin 92. However, in this embodiment, the second end 186 of the lever member 172 comprises an opening 196 sized and shaped to receive a pin 198 which is fixedly mounted to the housing 12. The movable connection between the opening 196 and the pin 198 allows for the lever member 172 to pivot (or rotate) about the pin 198.

Another difference in this embodiment is that the opening 188 is sized and shaped to receive the pin (or boss feature) 82 of the collar 68. According to some embodiments, the opening 188 comprises an elongated or slotted shape.

The mechanical arrangement 154 described above is configured to have the lever member 172 rotate (and/or slide) about the fixed pin 198 to transfer solenoid actuation to the inner blade tube 26. According to various exemplary embodiments, the solenoid motion (i.e. power stroke of solenoid 52 in direction 162) creates a forward motion (see arrow 99) of the inner blade tube 26. For example, when the solenoid 52 is actuated, the shaft 60 moves in direction 162, which causes the lever arm 172 to pivot or rotate about the pin 198, which further causes the collar 68 and the inner blade tube 26 to move in direction 99.

Similar to the mechanical arrangement 54, the mechanical arrangement 154 may comprise compression and/or expansion springs (between the collar and a bushing) to provide a biasing force for the reverse stroke. Additionally, in some other embodiments, the shaft 60 of the solenoid 52 could push directly on the collar 68. Also similar to the embodiment shown in FIG. 6, the openings 188, 194 have been described as having a slotted or elongated shape to provide "de-constrained" connections to pins 82, 92 while the connection between pin 198 and opening 196 provides for a substantially fixed pivot point. With this configuration the lever member 172 provides a swinging arc and a single fixed pivot point (at the movable connection between the pin 198 and the opening 196) and "de-constrained" connections (which move in x and y directions relative to the swinging arc [via the elongated/slotted openings 188, 194]) at pins 82, 92. However in alternate embodiments, the fixed pivot point could instead be provided at pin 82 or 92 with the "de-constrained" connections at the remaining two openings 188, 194, 196.

Technical effects of any one or more of the exemplary embodiments provide significant advantages over conventional configurations by providing greater force to the reciprocating blade than conventional air pressure-based devices can provide. A further technical effect of the various exemplary embodiments is providing a solenoid offset from the main blade to drive the blade directly by way of a flange affixed to the blade, or else indirectly by way of a rigid member on a pivot that reverses the direction of the force. Another technical effect of the various exemplary embodiments is that the blade is mounted with a spring in such a way that after each solenoid movement, the blade returns to its home position.

Figure 8:
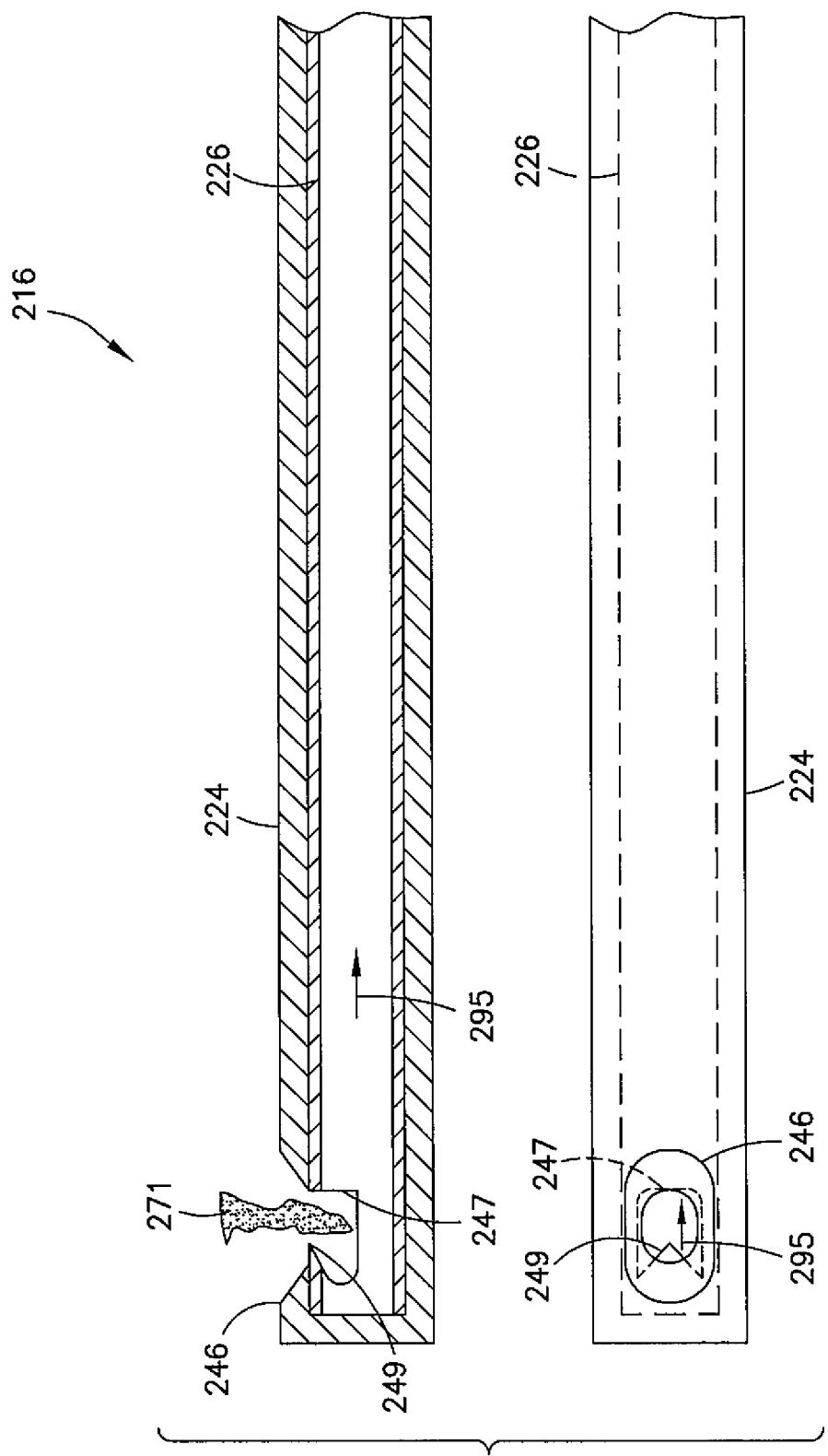
FIG. 8 is a section view and a top plan view of an alternate blade tube section used in the medical device shown in FIG. 1.

While various exemplary embodiments of the invention have been described in connection with a blade tube section 16 having a cutting edge 48 at the cutting window 46 of the outer blade tube 24, other configurations may be provided. For example, an alternate embodiment of a blade tube section 216 is shown in FIG. 8 (illustrating a cross-section view [top] and a top plan view [bottom]). Similar to the blade tube section 16, the blade tube section 216 comprises an outer blade tube 224 and an inner blade tube 226 configured to be driven by the blade drive system 28. However in this embodiment, the inner blade tube 226 comprises a cutting window 247 and a cutting edge 249. The cutting window 247 is configured to be aligned with the window 246 of the outer blade tube 224 such that the cutting is provided when tissue 271 extends through the windows 246, 247 and a backwards motion of the inner blade tube 226 (towards the proximate end [see arrow 295]) causes the cutting edge 249 to cut through the tissue 271.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: a blade tube section comprising an outer blade tube, an inner blade tube, and a cutting window at a distal end of the blade tube section; a solenoid offset from a central axis of the blade tube section; and a mechanical arrangement between the inner blade tube and the solenoid.

A medical device as above, wherein mechanical arrangement comprises a lever member, wherein the lever member is connected to the inner blade tube and the solenoid.

A medical device as above, further comprising a collar connected to the inner tube member.

A medical device as above, wherein the lever member is movably connected to the collar.

A medical device as above, wherein the mechanical arrangement is configured such that movement of a shaft of the solenoid in a first direction provides for movement of the inner blade tube in a second opposite direction.

A medical device as above, wherein the mechanical arrangement is configured such that movement of a shaft of the solenoid in a first direction provides for movement of the inner blade tube in the same direction.

A medical device as above, further comprising a collar, a bushing, and a spring, wherein the collar is connected to the inner tube member, and wherein the spring is between the bushing and the collar.

A medical device as above, wherein the inner blade tube is configured to reciprocate relative to the outer blade tube.

In another exemplary embodiment, a medical device comprising: a blade tube section comprising an outer blade tube, an inner blade tube, and a cutting window at a distal end of the blade tube section; a solenoid; and a lever member connected to the inner blade tube and the solenoid.

A medical device as above, wherein a mechanical arrangement is between the inner blade tube and the solenoid.

A medical device as above, further comprising a collar fixedly connected to the inner tube member.

A medical device as above, wherein the lever member is movably connected to the collar.

A medical device as above, wherein the lever member comprises a first end, a second end, and an opening between the first end and the second end, wherein the lever member is configured to rotate about the opening.

A medical device as above, wherein the lever member comprises a first end, a second end, and an opening between the first end and the second end, wherein the lever member is configured to rotate about the second end.

A medical device as above, further comprising a collar, a bushing, and a spring, wherein the collar is connected to the inner tube member, and wherein the spring is between the bushing and the collar.

A medical device as above, wherein the inner blade tube is configured to reciprocate relative to the outer blade tube.

A medical device as above, wherein the solenoid is offset from a central axis of the blade tube section.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
    a blade tube section comprising an outer blade tube, an inner blade tube, and a cutting window at a distal end of the blade tube section;
    a solenoid offset from a central axis of the blade tube section; and
    a mechanical arrangement between the inner blade tube and the solenoid, the mechanical arrangement including:
        a collar fixedly connected to the inner blade tube; and
        a lever member extending along a longitudinal axis and connected to the inner blade tube and the solenoid;
        wherein the lever member comprises a first end, a second end, and an elongated opening between the first end and the second end, the elongated opening having a length in a direction of the longitudinal axis that is greater than a width in a direction perpendicular to the longitudinal axis; and
        wherein the lever member is rotatable about the elongated opening and a pin to transfer solenoid actuation to the inner blade tube.

2. The medical device of claim 1 wherein the lever member is movably connected to the collar.

3. The medical device of claim 1 wherein the mechanical arrangement is configured such that movement of a shaft of the solenoid in a first direction provides for movement of the inner blade tube in a second opposite direction.

4. The medical device of claim 1 wherein the mechanical arrangement is configured such that movement of a shaft of the solenoid in a first direction provides for movement of the inner blade tube in the same direction.

5. The medical device of claim 1 wherein the mechanical arrangement further comprises a bushing and a spring, wherein the spring is between the bushing and the collar.

6. The medical device of claim 1 wherein the inner blade tube is configured to reciprocate relative to the outer blade tube.

7. A medical device comprising:
    a housing;
    a blade tube section comprising an outer blade tube, an inner blade tube, and a cutting window at a distal end of the blade tube section;
    a collar fixedly connected to the inner blade tube;
    a solenoid; and
    a lever member extending along a longitudinal axis and comprising a first end connected to the inner blade tube at a first connection and a second end connected to the solenoid at a second connection;
    wherein the second connection comprises an elongated slot and a pin; and
    wherein the lever member is connected to the housing at a third connection, the third connection comprising an elongated slot between the first end and the second end of the lever member and a pin or boss member fixedly mounted to the housing, the elongated slot having a length in a direction of the longitudinal axis that is greater than a width in a direction perpendicular to the longitudinal axis.

8. The medical device of claim 7 wherein the lever member is movably connected to the collar.

9. The medical device of claim 7 wherein the lever member is configured to rotate about the second end.

10. The medical device of claim 7 further comprising a bushing and a spring, wherein the spring is between the bushing and the collar.

11. The medical device of claim 7 wherein the inner blade tube is configured to reciprocate relative to the outer blade tube.

12. The medical device of claim 7 wherein the solenoid is offset from a central axis of the blade tube section.

* * * * *